(12) United States Patent
Matsuo et al.

(10) Patent No.: US 7,354,996 B2
(45) Date of Patent: Apr. 8, 2008

(54) METHOD AND KIT FOR QUANTITATIVE ANALYSIS OF PROTEIN

(75) Inventors: Eiichi Matsuo, Kyoto (JP); Makoto Watanabe, Osaka (JP); Chikako Toda, Kyoto (JP); Osamu Nishimura, Kawanishi (JP)

(73) Assignee: Shimadzu Corporation, Kyoto (JP)

( * ) Notice: Subject to any disclaimer, the term of this patent is extended or adjusted under 35 U.S.C. 154(b) by 312 days.

(21) Appl. No.: 11/028,322

(22) Filed: Jan. 4, 2005

(65) Prior Publication Data
US 2006/0051831 A1 Mar. 9, 2006

(30) Foreign Application Priority Data
Sep. 7, 2004 (JP) ............................... 2004-259855

(51) Int. Cl.
*A61K 38/00* (2006.01)
(52) U.S. Cl. ...................... 530/344; 530/335; 250/282
(58) Field of Classification Search ..................... None
See application file for complete search history.

(56) References Cited

U.S. PATENT DOCUMENTS

2005/0224710 A1* 10/2005 Matsuo et al. .............. 250/288

FOREIGN PATENT DOCUMENTS

| EP | 0 419 081 A2 | 3/1991 |
|---|---|---|
| EP | 1 533 296 A1 | 5/2005 |
| JP | 2000-023684 A | 1/2000 |
| JP | 2003-098151 | 4/2003 |
| JP | 2004-081042 A | 3/2004 |
| WO | WO-2004/002950 A1 | 1/2004 |

OTHER PUBLICATIONS

Kuyama H et al (2003) An approach to quantitative proteome analysis by labeling tryptophan residues. Rapid Commun Mass Spectrom, vol. 17, pp. 1642-1650.*
Walsh MP et al (1984) Ca2+-dependent hydrophobic-interaction chromatography. Biochem J, vol. 224, pp. 117-127.*
Yu Y-Q et al (2003) Enzyme-friendly, mass spectrometry-compatible surfactant for in-solution enzymatic digestion of proteins. Anal Chem, vol. 75, pp. 6023-6028.*
Yang HH et al (1998) Protein conformational changes determined by matrix-assisted laser desorption mass spectrometry. Anal Biochem, vol. 258, pp. 118-126.*
PCT Notification Concerning Transmittal of Copy of International Preliminary Examination Report on Patentability Chapter I of the Patent Cooperation Treaty dated Oct. 26, 2006 with English Translation.

M.E. Gimon, et al., "Are Proton Transfer Reactions of Excited States Involved in UV Laser Desorption Ionization?", Organic Mass spectrometry, 1992, vol. 27, No. 7, pp. 827-830.
Michael C. Fitzgerald , et al., "Basic Matrices for the Matrix-Assisted Laser Desorption/Ionization Mass Spectrometry of Proteins and Oligonucleotides", Analytical Chemistry, 1993, vol. 65, No. 22, pp. 3204-3211.
Green-Church K B and Limbach P A, "Matrix-Assisted Laser Desorption/Ionization Mass Spectrometry of Hydrophobic Peptides", Analytical Chemistry, 1998. 12.15, vol. 70, No. 24, pp. 5322-5325.
PCT International Search Report for PCT/JP2005/006890 mailed on Jun. 25, 2005.
Steven P. Gygi, et al., Quantitative analysis of complex protein mixtures using isotope-coded affinity tags, Nature Biotechnology, vol. 17, Oct. 1999, pp. 994-999, http://www.biotech.nature.com.
Kirk C. Hansen, et al., Mass spectrometric analysis of protein mixtures at low levels using cleavable $^{13}C$-isotope-coded affinity tag and multidimensional chromatography, Molecular & Cellular Proteomics 2.5, pp. 299-314, Feb. 2003, http://www.mcponline.org.
Salvatore Sechi, et al., Quantitative proteomics using mass spectrometry, Current Opinion in Chemical Biology, pp. 70-77, Jul. 2003, http://www.current-opinion.com.
Hiroki Kuyama, et al., An approach to quantitative proteome analysis by labeling tryptophan residues, Rapid Communications in Mass Spectrometry, pp. 1642-1650, Jul. 2003, http://www.intersciences.siley.com.

* cited by examiner

*Primary Examiner*—Ralph Gitomer
(74) *Attorney, Agent, or Firm*—Cheng Law Group PLLC

(57) ABSTRACT

The present invention provides a method for global quantitative analysis of protein that is effectively applied also for unpurified samples such as biological samples, and achieves better detection sensitivity and quantitativeness than the conventional NBS method. A method for global quantitative analysis of protein comprising: preparing two states of protein samples, a Protein sample I for analysis and a control Protein sample II; solubilizing the Protein sample I and II by urea or guanidine hydrochloride; subjecting the solubilized Protein sample I and II to modification using 2-nitro[$^{13}C_6$] benzenesulfenyl chloride and 2-nitro[$^{12}C_6$]benzenesulfenyl chloride; mixing and desalting the modified Protein sample I and II; resolubilizing by urea or guanidine hydrochloride; reducing and alkylating; subjecting to trypsin digestion in the presence of urea or guanidine hydrochloride; separating the obtained peptide mixture using a media having a phenyl group; and subjecting the enriched modified peptide fragments to mass spectrometry preferably using 3CHCA, 3H4NBA or mixture of 3H4NBA and 4CHCA as a matrix.

12 Claims, 9 Drawing Sheets

METHOD AND KIT FOR QUANTITATIVE ANALYSIS OF PROTEIN

BACKGROUND OF THE INVENTION

1. Field of the Invention

The present invention relates to a proteome analysis (global analysis of protein) using a stable isotope.

2. Disclosure of the Related Art

In the field of proteome analysis (global analysis of protein), a PMF (Peptide Mass Finger Printing) analysis method in which a two-dimensional gel electrophoresi's and a mass spectrometer are combined is commonly used. As a next-generation proteome analysis method which will be an alternative to the PMF, for example, approaches using stable isotopes as disclosed in: Steven P. Gygi, Beate Rist, Scott A. Gerber, Frantisek Turecek, Michael H. Gelb and Ruedi Aebersold, Quantitative analysis of complex protein mixtures using isotope-coded affinity tags, Nature Biotechnology, 994-999, 17, 1999; Kirk C. Hansen, Gerold Schmitt-Ulms, Robert J. Chalkley, Jan Hirsch, Michael A. Baldwin and A. L. Burlingame, Mass Spectrometric Analysis of Protein Mixtures at Low Levels Using Cleavable $^{13}$C-Isotope-coded Affinity Tag and Multidimensional Chromatography, Molecular & Cellular PROTEOMICS, 299-314, 2, 2003; and, Salvatore Sechi and Yoshiya Oda, Quantitative proteomics using mass spectrometry, Current Opinion in Chemical Biology, 70-77, 7, 2003 have been contrived.

In Hiroki Kuyama, Makoto Watanabe, Chikako Toda, Eiji Ando, Koichi Tanaka and Osamu Nishimura, An Approach to Quantitative Proteome Analysis by Labeling Tryptophan Residues, Rapid Communications in Mass Spectrometry, 1642-1650, 17, 2003, and the international publication WO 2004/002950 pamphlet, a method developed by the present inventors (NBS method) is disclosed. The NBS method uses stable isotope-labeled 2-nitrobenzenesulfenyl chloride (NBSCl) (2-nitro [$^{13}C_6$] benzenesulfenyl chloride) and unlabeled NBSCl (2-nitro [$^{12}C_6$] benzenesulfenyl chloride). Specifically, the method includes the steps of: (1) preparing two states of protein samples, a protein sample I to be analyzed and its reference protein sample II; (2) modifying the protein sample I with either one of 2-nitro [$^{13}C_6$] benzenesulfenyl chloride and 2-nitro [$^{12}C_6$] benzenesulfenyl chloride, while modifying the protein sample II with the other one of 2-nitro [$^{13}C_6$] benzenesulfenyl chloride and 2-nitro [$^{12}C_6$] benzenesulfenyl chloride; (3) mixing the modified protein sample I and the modified protein sample II with each other; (4) subjecting the resultant mixture of modified proteins to reduction and alkylation followed by digestion into a peptide mixture containing modified peptide fragments and unmodified peptide fragments; (5) enriching/separating the modified peptide fragments from the peptide mixture by using a hydrophobic chromatography column; and (6) conducting mass spectrometry.

One exemplary protocol of NBS method will be described below.

Solubilize two series of protein samples, a test sample and a control sample, respectively, in a solution containing 0.1 w/v % SDS, and denature by heating (100° C., 3 min.).

Add an acetic acid solution dissolving NBS (Heavy) reagent to one of the samples, and an acetic acid solution dissolving NBS (Light) reagent to the other of the samples, to cause NBS modification reaction respectively (room temperature, overnight).

Mix both of the samples and remove unreacted reagents using a desalting column (LH-20).

Dry the sample after desalting and resuspend in a solution containing 0.01 w/v % SDS.

Add TCEP (Tris(2-carboxyethyl)phosphine hydrochloride) to cause reductive reaction (37° C., 30 min.).

Add an iodoacetamide solution to cause alkylation reaction (room temperature, 45 min.).

Add trypsin to cause site-specific cleavage (37° C., 16 hours).

Enrich NBS-modified peptides using an enrichment column (LH-20).

Analyze enriched fractions using a mass spectrometer.

SUMMARY OF THE INVENTION

A conventional NBS method developed by the present inventors is especially effectively applied when purified samples such as protein model are used. In order to provide a method for global quantitative analysis of protein that is effectively applied not only for purified samples as described above but also for unpurified samples such as biological samples, and achieves better detection sensitivity and quantitativeness than the conventional NBS method, the inventors of the present application accomplished the present invention.

The present invention encompasses the following aspects.

(1) A method for global quantitative analysis of protein comprising the steps of:

(i) preparing two states of protein samples, a Protein sample I for analysis and a control Protein sample II;

(ii) solubilizing the Protein sample I in a solution containing urea as a denaturing agent or in a solution containing guanidine hydrochloride as a denaturing agent, to obtain a solubilized Protein sample I, and separately solubilizing the Protein sample II in a solution containing urea as a denaturing agent or in a solution containing guanidine hydrochloride as a denaturing agent, to obtain a solubilized Protein sample II;

(iii) subjecting the solubilized Protein sample I to modification reaction using either one of 2-nitro[$^{13}C_6$]benzenesulfenyl chloride and 2-nitro[12 $C_6$]benzenesulfenyl chloride, to obtain a modified Protein sample I, and separately subjecting the solubilized Protein sample II to modification reaction using the other one of 2-nitro[$^{13}C_6$] benzenesulfenyl chloride and 2-nitro[$^{12}C_6$]benzenesulfenyl chloride, to obtain a modified Protein sample II;

(iv) mixing and desalting the modified Protein sample I and the modified Protein sample II, to obtain a desalted protein sample mixture;

(v) resolubilizing the desalted protein sample mixture by using urea or guanidine hydrochloride, to obtain a resolubilized protein sample mixture;

(vi) reducing and alkylating the resolubilized protein sample mixture, to obtain a reduced and alkylated protein sample mixture;

(vii) subjecting the reduced and alkylated protein sample mixture to trypsin digestion in the presence of urea or guanidine hydrochloride, to obtain a peptide mixture containing modified peptide fragments and unmodified peptide fragments;

(viii) separating the peptide mixture using a media having a phenyl group, to obtain enriched modified peptide fragments; and (ix) subjecting the enriched modified peptide fragments to mass spectrometry.

(2) The method according to the above (1), wherein in the step (ix), the mass spectrometry is conducted using α-cyano-3-hydroxycinnamic acid or 3-hydroxy-4-nitrobenzoic acid as a matrix.

(3) The method according to the above (1), wherein in the step (ix), when 3-hydroxy-4-nitrobenzoic acid is used as the matrix, the mass spectrometry is conducted using a mixed matrix of 3-hydroxy-4-nitrobenzoic acid and α-cyano-4-hydroxycinnamic acid.

(4) The method according to the above (2) or (3), wherein the matrix is used as a solution having a concentration of 1 mg/ml to a saturated concentration.

(5) The method according to the above (3) or (4), wherein α-cyano-4-hydroxycinnamic acid is used as a solution having a concentration of 1 mg/ml to a saturated concentration.

(6) The method according to the above (5), wherein the solution of 3-hydroxy-4-nitrobenzoic acid and the solution of α-cyano-4-hydroxycinnamic acid are combined in a volume ratio of 1:10 to 10:1 to be used.

(7) A kit containing 2-nitro[$^{13}C_6$]benzenesulfenyl chloride, 2-nitro[$^{12}C_6$]benzenesulfenyl chloride, and a media having a phenyl group.

(8) A kit for carrying out the method according to any one of the above (1) to (6), containing 2-nitro [$^{13}C_6$]benzenesulfenyl chloride, 2-nitro[$^{12}C_6$]benzenesulfenyl chloride, and a media having a phenyl group.

(9) The kit according to the above (7) or (8), further containing a denaturing agent.

(10) The kit according to any one of the above (7) to (9), further containing α-cyano-3-hydroxycinnamic acid, 3-hydroxy-4-nitrobenzoic acid, or α-cyano-4-hydroxycinnamic acid as a matrix, or a mixture of 3-hydroxy-4-nitrobenzoic acid and α-cyano-4-hydroxycinnamic acid as a mixed matrix.

(11) The kit according to the above (9) or (10), wherein the denaturing agent is urea or guanidine hydrochloride.

(12) The kit according to any one of the above (7) to (11), further containing at least one selected from the group consisting of a desalting column, filling gel for a desalting column, a reduction reagent, an alkylation reagent, trypsin, and a column for filling the media.

According to the present invention, a method capable of detecting an objective peptide from a biological sample with better sensitivity and quantitativeness in mass spectrometry can be provided.

DETAILED DESCRIPTION OF THE INVENTION

Figure 1:
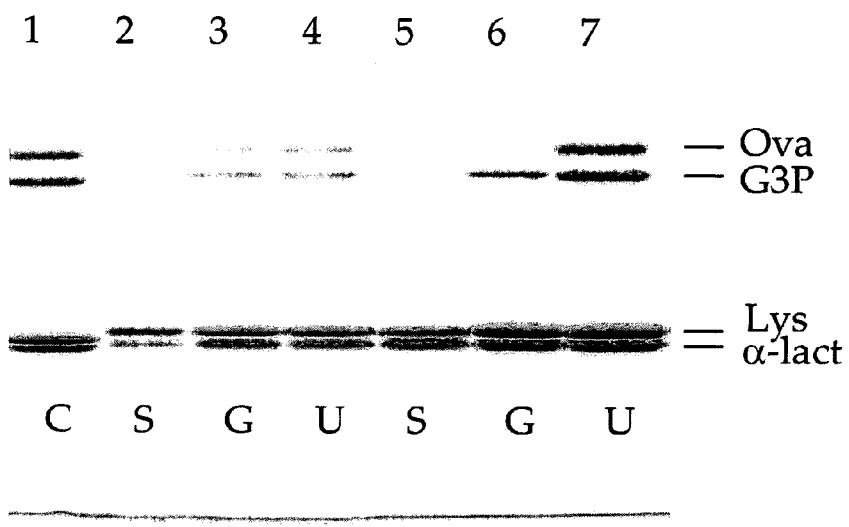
FIG. 1 is an electrophoretic diagram obtained in Experimental Example 1.

The method of the present invention includes sample preparation step (i); solubilization step (ii); modification step (iii); desalting step (iv); resolubilization step (v); reduction and alkylation step (vi); digestion step (vii); enrichment/separation step (viii); and mass spectrometry step (xi).

(i: Sample Preparation Step)

First, prepare two different states of Protein samples I and II. For example, Protein sample I may be a protein sample to be analyzed and Protein sample II may be a sample containing the control proteins for the protein contained in Protein sample I. More concretely, Protein sample I for analysis may be a protein sample of pathologic state, and control Protein sample II may be a protein sample of normal state. In the present invention, quantitative analysis of expressed proteomes between these Protein sample I and Protein sample II is performed. In the present invention, the protein samples may include molecules having a relatively low molecular weight such as peptides.

(ii: Solubilization Step)

This step is conducted individually on Protein sample I and Protein sample II under the same condition.

In this step, a protein sample is solubilized using urea or guanidine hydrochloride which is a denaturing agent. Concentration of the denaturing agent is not particularly limited, and may be appropriately determined by the one skilled in the art in consideration of the kind of the protein sample, other conditions or the like, so as to make the protein sample solubilize and denature. For example, urea may be used in an aqueous solution having a concentration of 2 M to a saturated concentration, preferably 2 M to 10 M. More preferably, urea is used in an aqueous solution of 8 M. Guanidine hydrochloride may be used in an aqueous solution having a concentration of 1.5 M to a saturated concentration, preferably 1.5 M to 8 M. More preferably, guanidine hydrochloride is used in an aqueous solution of 6 M. Moreover, the denaturing agent may be used in combination with EDTA of about 5 mM.

Further, the above denaturing agents may be used in such an amount that the denaturing agent is 5 to 50 μl per 100 μg of the protein sample. A preferred amount is about 25 μl. For example, when the protein sample is in a freeze-dried powder state, 25 μl of denaturing agent may be used, while when the protein sample is a solution state, the denaturing agent may be used with the concentration of the denaturing agent adjusted so that the final volume is 25 μl.

A temperature of solubilization may be 0 to 30° C., preferably at about room temperature when urea is used; and at a temperature of 0 to 100° C., preferably at about room temperature when guanidine hydrochloride is used.

(iii: Modification Step)

In this step, the protein samples solubilized in the manner as described above are modified using two modification reagents, namely isotope-labeled 2-nitro[$^{13}C_6$]benzenesulfenyl chloride (NBSCl(heavy)) and isotope-unlabeled 2-nitro[$^{12}C_6$]benzenesulfenyl chloride (NBSCl(light)). These modification reagents of the present invention selectively modify, namely label a tryptophan residue in a protein. Protein sample I is modified with either one of NBSCl (heavy) and NBSCl(light), and separately from this, Protein sample II is modified with the other one of NBSCl(heavy) and NBSCl(light).

The modification reagent is preferably used as a solution of acetic acid. For example, a solution dissolving 0.17 mg of 2-nitrobenzenesulfenyl chloride in 25 µl of acetic acid may be used. Such a modification reagent may be used in great excess amount of about 20 equivalents of the protein sample. For example, with respect to 100 µg of the protein sample, a modification reagent solution may be used so as to contain 0.17 mg of 2-nitrobenzenesulfenyl chloride. In this way, quite nearly 100% of tryptophan residues in the protein sample are modified.

Strictly speaking, 2-nitrobenzenesulfenyl chloride strictly has a difference in molecular mass of about 3% between the NBSCl(light) and the NBSCl(heavy). However, when mass of 2-nitrobenzenesulfenyl chloride is described herein, the difference in mass of these substances at the same molar amount is regarded as calculationally negligible. Therefore, the same mass may used for these two substances.

The modification reaction may be conducted by adding a modification reagent to protein samples, and incubation. About four hours is sufficient for allowing the reaction. In other words, the reaction may be ended right after starting of the reaction or within four hours. The standard protocol may employ a reaction time of one hour.

In this manner, the present invention significantly reduces the modification reaction time compared to the conventional NBS method. For this reason, it becomes possible to shorten the operation time required for executing the overall protocol of three days, in turn, to two days.

(iv: Desalting Step)

In this step, the modified Protein sample I and the modified Protein sample II obtained in the above step (iii) are mixed, and then the resultant protein sample mixture is subjected to desalting. As a desalting method, any conventional method may be used without any restriction. For example, desalting may be conducted using a Sephadex LH-20 column and an aqueous solution of acetonitrile.

(v: Resolubilization Step)

In this step, the desalted protein sample mixture obtained in the above step (iv) is resolubilized using urea or guanidine hydrochloride serving as a denaturing agent. The concentration of the denaturation agent is not particularly limited, and may be appropriately determined by one skilled in the art in consideration of the kind of the protein sample, other conditions or the like so that the solubilization and the denaturing of the protein sample will occur. For example, urea may be used as an aqueous solution having a concentration of 2 M to a saturated concentration, preferably 2 M to 10 M. More preferably, urea is used as an aqueous solution of 8 M. Guanidine hydrochloride may be used as an aqueous solution having a concentration of 1.5 M to a saturated concentration, preferably 1.5 M to 8 M. More preferably, guanidine hydrochloride is used as an aqueous solution of 6 M. In the present step, Tris HCl (pH approx. 8.8) of about 50 mM is added as a buffer for the purpose of pH adjustment in the subsequent reduction and alkylation step.

In the present invention, the conditions defined in the above solubilization step (ii) and the resolubilization step (v) can avoid the problem of aggregation that have often occurred in protein samples conventionally. Therefore, it is possible to keep the solubility until the later-described digestion step (vii) with least loss of sample. The later described Experimental Example 1 and Experimental Example 2 practically demonstrated such an effect.

As described above, since the method of the present invention can significantly reduce the sample loss compared to the conventional NBS method, the coverage of NBS modified peptide ion detected in mass spectrometry is dramatically improved. This effect enables the present invention to be usefully applied in analysis of, in particular, samples derived from living organism such as sera or extracts from organs. The later-described Experimental Example 3 practically demonstrated such an effect.

Furthermore, the present invention significantly improves the quantitativeness compared to the conventional NBS method. The later described Experimental Example 4 practically demonstrated such an effect.

(vi: Reduction and Alkylation Step)

In this step, conventional reagents and reaction conditions may be used without any restriction. Alkylation mainly occurs at a sulfhydryl group, however, alkylation may also occur at an imidazolyl group, an amino group or the like. Therefore, in the conventional NBS method, alkylation will occur not only at an amino acid residue having a sulfhydryl group such as cysteine, but also partially occur at an amino acid residue having other amino groups in some cases. As a result, a peak larger by m/z value of 57 than a peak of objective peptide (+57(m/z) peak) is sometimes observed in a mass spectrum. While in the present invention, a reaction solution of this step contains urea or guanidine hydrochloride. These substances have an amino group. Partial alkylation that has conventionally occurred at other amino acid residues having an imidazolyl group or an amino group would occur at an amino group of urea or guanidine hydrochloride which is present in the reaction system of the present invention. In other words, alkylation which is a side reaction occurred in the conventional method would be competitively inhibited. As a result, in the present invention, the aforementioned +57(m/z) peak is hardly detected in a mass spectrum. The later-described Experimental Example 5 practically demonstrated such an effect.

(vii: Digestion Step)

In this step, trypsin digestion is conducted. This step is conducted in the presence of urea or guanidine hydrochloride which is a denaturing agent. The concentration of the denaturing agent may be 0.08 M to 4 M, preferably 0.8 M to 1.6 M in the case of urea, and 0.06 M to 3 M, preferably 0.6 M in the case of guanidine hydrochloride. In this step, $CaCl_2$ of approx. 5 mM is preferably added for the purpose of stabilization of trypsin structure and its activation.

In the present step, the denaturing agent remaining in the sample of the above resolubilization step is available. For example, a trypsin digestion buffer may be added to the sample after completion of the resolubilization step and the reduction and alkylation step so that a desired concentration is achieved. As other conditions for digestion, pH is adjusted so as to be around the optimum pH of trypsin enzyme, and reaction time may be about 4 to 16 hours at 37° C. normally. In this manner, a peptide mixture containing modified peptide fragments and unmodified peptide fragments is obtained.

(viii: Enrichment/Separation Step)

In this step, modified peptides are selectively enriched from the above peptide mixture using a media having a phenyl group. This step utilizes the unique selectivity due to the π-π electrons interaction acting between π-electron compounds. To be more specific, the media exerts excellent retention ability to the modified peptide through the interaction between a π electron possessed by an indole group of tryptophan and a nitrophenylthio group in the modified peptide and a π electron possessed by a phenyl group on the media, allowing selective enrichment and separation. Such a media is appropriately selected from Hi-Trap phenyl FF, Hi-Trap phenyl HP, Phenyl Sepharose 6 Fast Flow, Phenyl Sepharose High Performance (there are available from Amersham Biosciences), YMC*GEL Ph (YMC Corporation) and the like, and used as a phenyl column.

On the other hand, in the conventional NBS method using a LH-20 column, a significant number of unmodified peptides were mingled in an eluted fractions. According to the present invention, the number of mingled unmodified peptides is decreased, and especially, unmodified peptides detected around m/z value of 1200-1700 that are observed a lot in the conventional NBS method are hardly observed. Additionally, in the conventional NBS method, each of peptides is eluted in almost all of the eluted fractions in the enrichment/separation step, while the present invention can separate the each of peptides each other to some extent. Accordingly, the present invention is superior in coverage of detected peptides to the conventional method. The later-described Experimental Example 6 practically demonstrated such an effect.

(ix: Mass Spectrometry Step)

The modified peptides enriched and separated in the above step (viii) are subjected to mass spectrometry. When a MALDI mass spectrometer is used in measurement of the present invention, a MAIDI-IT-TOF mass spectrometer (for example, AXIMA-QIT available from SHIMADZU) and the like may be used in addition to the MALDI-TOF mass spectrometer (for example, AXIMA-CFR, available from SHIMADZU) used in the conventional NBS method.

When a MALDI-TOF mass spectrometer is used, 4-CHCA (α-cyano-4-hydroxycinnamic acid) or the like is used as a matrix. On the other hand, when a MAIDI-IT-TOF mass spectrometer is used, 3-CHCA (α-cyano-3-hydroxycinnamic acid) or 3H4NBA (3-hydroxy-4-nitrobenzoic acid) is used as a matrix.

A person skilled in the art may appropriately determine the use form of these compounds in view of the use as a matrix for mass spectrometry. For example, these compounds are preferably used in a solution state. For example, the solution may be used at a concentration of 1 mg/ml to a saturated concentration.

Preferred solvents used in preparing the above solution include an aqueous solution of acetonitrile, an aqueous solution of trifluoroacetic acid (TFA), or an aqueous solution of acetonitrile-trifluoroacetic acid (TFA). When the aqueous solution of acetonitrile or the aqueous solution of acetonitrile-TFA is used, the concentration of acetonitrile may be, but not limited to, not more than 90%, preferably about 50%. When the aqueous solution of TFA or the aqueous solution of acetonitrile-TFA is used, the concentration of TFA may be, but not limited to, not more than 1%, preferably about 0.1%.

As for 4-CHCA, 4-CHCA is dissolved in the above solvent and may be used as a matrix solution having a concentration of 1 mg/ml to a saturated concentration, preferably 10 mg/ml.

As for 3-CHCA, 3-CHCA is dissolved in the above solvent and may be used as a matrix solution having a concentration of 1 mg/ml to a saturated concentration, preferably 10 mg/ml.

Further, as for 3H4NBA, 3H4NBA is dissolved in the above solvent and used as a matrix solution having a concentration of 1 mg/ml to a saturated concentration, preferably a saturated concentration.

The amount expressed as % in this description is on the basis of v/v % unless otherwise specified.

In identifying a sequence of a peptide existing at different abundances in different samples, MS/MS analysis using a mass spectrometer equipped with a quadrupole ion trap (QIT) such as an AXIMA-QIT (available from SHIMADZU) is more favorable than PSD analysis by an AXIMA-CFR (available from SHIMADZU) from the view point of sensitivity. In measurement using such an ion trap type mass spectrometer, DHB (2,5-dihydroxy benzoic acid) is usually used as a matrix. However, when DHB is used as a matrix, NBS-modified peptides are hardly detected. Accordingly, 3-CHCA or 3H4NBA is used as a matrix when measurement is conducted using an ion trap type mass spectrometer in the present invention. This enables efficient ionization of NBS-modified peptides. Therefore, the efficiency of MS/MS analysis of NBS-modified peptides in the present invention is dramatically improved in comparison with the conventional NBS method. The later-described Experimental Example 7 practically demonstrated such an effect.

In the present invention, when 3-hydroxy-4-nitrobenzoic acid (3H4NBA) is used as a matrix, 3H4NBA is preferably used as a mixed matrix in which 3H4NBA is combined with α-cyano-4-hydroxycinnamic acid (4-CHCA). (Hereinafter, a singularly used matrix in which the matrix is used without combining with 4-CHCA, and a mixed matrix in which 4-CHCA is used in combination are sometimes simply described as matrix.)

3H4NBA and 4-CHCA may be combined, for example, in the following quantitative relationship in a nonrestrictive manner.

3H4NBA may be prepared at a concentration as described above. Specifically, a 3H4NBA solution may be prepared as an aqueous solution having a concentration of 1 mg/ml to a saturated concentration; for example, when an aqueous solution of acetonitrile, an aqueous solution of TFA, or an aqueous solution of acetonitrile-TFA is used as a solvent, a 3H4NBA solution may be prepared as a solution having a concentration of 1 mg/ml to a saturated concentration, preferably a saturated concentration.

On the other hand, 4-CHCA may also be prepared at a concentration as described above. Specifically, a 4-CHCA solution may be prepared as an aqueous solution having a concentration of 1 mg/ml to a saturated concentration; for example, when an aqueous solution of acetonitrile, an aqueous solution of TFA, or an aqueous solution of acetonitrile-TFA is used as a solvent, 4-CHCA solution may be prepared as a solution having a concentration of 1 mg/ml to a saturated concentration, preferably 10 mg/ml.

The both of solution prepared in these manners are mixed in a volume ratio of, preferably 1:10 to 10:1, more preferably 1:3 to 3:1, for example 1:1 for use.

The conventional matrix 4-CHCA has a drawback that self-disintegration of an analyte to be measured occurs during measurement with a MALDI spectrometer such as MALDI-IT, MALDI-IT-TOF, or MALDI-FTICR spectrometer in which a time from ionization to detection of ion is long. However, the conventional matrix 4-CHCA shows excellent measuring sensitivity and is advantageous in that an optimum spot on which a laser is to be focused can be easily found in a mass spectrometric sample.

On the other hand, the matrix 3H4NBA of the present invention can advantageously suppress the progression of self-disintegration of an analyte to be measured, and achieve specific ionization of a hydrophobic analyte, especially of a NBS-modified peptide. The matrix 3H4NBA of the present invention is used in combination with 4-CHCA, thereby synergistic effect of the advantages given by both of the matrices is exerted. In brief, an ability to detect with high sensitivity possessed by 4-CHCA is added while maintaining an ability to detect with specificity possessed by 3H4NBA by itself, and achievability of ionization of hydrophobic sample, and it is possible to conduct a mass spectrometry with higher analytical efficiency. The later-described Experimental Examples 8 and 9 practically demonstrated such an effect.

A concrete protocol of the present invention will be described below. This protocol is described for treating each 10 μg of the samples in states I and II. (NBSCl and NBS-modified peptides should be kept from light as much as possible during this protocol.) As is already mentioned, any amount expressed by % in this protocol and later-described Experimental Examples is based on v/v % unless otherwise specified.

[Solubilization of Ample (Separately Executed for Samples of State I and state II]
1. Prepare each 100 μg of samples of "state I" and "state II".
2. Lyophilize each sample (or dry to solid using a vacuum concentrator).
3. Dissolve each sample in 25 μl of a denaturing buffer (8 M aqueous solution of urea containing 5 mM EDTA, or 6 M aqueous solution of guanidine hydrochloride containing 5 mM EDTA).
4. Stir well on a Vortex mixer.

[Modification of Tryptophan Residue with NBSCl (Separately Executed for Samples of State I and State II)]
1. Add 25 μl of NBS reagent (light) solution (acetic acid solution containing 0.17 mg of NBSCl(light)) to the sample of "state I", and stir on a Vortex mixer, separately add 25 μl of NBS reagent (heavy) solution (acetic acid solution containing 0.17 mg of NBSCl(heavy)) to the sample of "state II", and stir on a Vortex mixer.
2. Incubate each sample for one hour under gentle stirring.

[Desalting of Reaction Solution and Removal of Excess NBS Reagent (the Two Modified Samples are Mixed in this Step)]
1. Prepare an LH-20 column (equilibrate 500 μl of LH-20 in advance with 30% acetonitrile aqueous solution), and allow the supernatant to freely fall to the level of the resin layer.
2. Gently apply a mixed sample (mixture of NBSCl (light)-modified sample and NBSCl(heavy)-modified sample, total volume 100 μl) on the column. (Discard flow-through fractions.)
3. Wash the column with 100 μl of 30% acetonitrile aqueous solution.
4. Elute the desalted sample with 200 μl of 30% acetonitrile aqueous solution.
5. Lyophilize the eluted fractions.

[Reduction and Alkylation]
1. Dissolve the sample in 48 μl of 8 M aqueous solution of urea containing 50 mM Tris HCl (pH8.8) or 6 M aqueous solution guanidine hydrochloride containing 50 mM Tris HCl (pH8.8).
2. Add 1 μl of a reduction solution (200 mM TCEP aqueous solution) and gently stir.
3. Incubate for 30 min. at 37° C.
4. Add 1 μl of an alkylation solution (500 mM iodoacetamide aqueous solution) and gently stir.
5. Incubate at room temperature for 45 min.

[Trypsin Digestion]
1. Dissolve 10 μg of trypsin (Promega, sequencing grade) in 450 μl of a digestion buffer (50 mM Tris HCl (pH7.8), 5 mM $CaCl_2$).
2. Add the trypsin solution to the sample and gently mix by pipetting.
3. Incubate at 37° C. for 4 to 16 hours.
4. Add 50 μl of 1% TFA aqueous solution (final concentration 0.1%) before loading on the column. Hydrochloric acid may be added in place of TFA. In such a case, the hydrochloric acid may be adjusted so that its final concentration is 10 mM.

[Enrichment of Modified Peptides]
1. Fill an open column with 1 ml of phenyl column such as Phenyl Sepharose™ High Performance (Amersham Biosciences).
2. Equilibrate the column with 5 ml of water, followed by 5 ml of 0.1% TFA aqueous solution.
3. Apply 550 μl of digested sample on the column (collect this eluate as "Flow-through" fraction).
4. Wash the column with 1 ml of 0.1% TFA aqueous solution (collect this eluate as "Wash" fraction).
Repeat this step twice more (three times in total).
5. Elute with 0.5 ml of an elution buffer (0.1% TFA aqueous solution containing 10% acetonitrile) (collect this eluate as "Elute" fractions), and repeat this step once more.
6. Repeat the step 5. until the concentration of acetonitrile is 40% while increasing the concentration of acetonitrile by 5% at a time.
7. (Optional step: conduct as necessary). For MS analysis, desalt and enrich peptides from the "Flow-through" fraction and "Wash" fractions using ZipTip.
8. Dry the "Elute" fractions to solid by means of a vacuum concentrator. For MS analysis or further separation using HPLC or the like, suspend the dried solid sample in about 5 to 50 μl of 0.1% TFA aqueous solution.

Hydrochloric acid may be used in place of the 0.1% TFA aqueous solution used in enrichment of the modified peptides. In this case, the hydrochloric acid may be adjusted so that its concentration is 10 mM.

[Mass Spectrometry]
The sample may be directly subjected to MS analysis, or may be further fractionated using HPLC and the like. When MALDI-MS measurement is conducted, the sample is mixed with a matrix solution for conducting MS measurement.

The present invention further provides a kit containing 2-nitro[$^{13}C_6$]benzenesulfenyl chloride, 2-nitro[$^{12}C_6$]benzenesulfenyl chloride, and a media having a phenyl group.

These 2-nitro [$^{13}C_6$]benzenesulfenyl chloride and 2-nitro [$^{12}C_6$]benzenesulfenyl chloride may be used, for example, as modification reagents for conducting the above modification step (iii). The media having a phenyl group may be used for conducting the above enrichment/separation step (viii).

Therefore, the kit of the present invention may be used for conducting a global quantitative analysis of protein, for example, the protocol described above.

More specifically, the kit of the present invention contains 2-nitro [$^{13}C_6$]benzenesulfenyl chloride (NBSCl(heavy); NBS(heavy) reagent) and 2-nitro [$^{12}C_6$]benzenesulfenyl chloride (NBSCl(light); NBS(light) reagent) serving as modification reagents for conducting the above modification step (iii) and a media having a phenyl group for conducting the above enrichment/separation step (viii), and preferably includes a denaturing agent and/or a matrix. The kit of the present invention may contain various solvents used in the method of the present invention as described above.

The denaturing agent may be used for conducting the above solubilization step (ii) and the above resolubilization step (v). Therefore, as the denaturing agent, urea or guanidine hydrochloride as described in the solubilization step (ii) and the resolubilization step (v) is preferably used. The denaturing agent may be dissolved in solvents described in the solubilization step (ii) and the resolubilization step (v). For example, when guanidine hydrochloride is employed as a denaturing agent, it may be provided as it is dissolved in a solvent. In such a case, guanidine hydrochloride may be an aqueous solution having a concentration of 1.5 M to saturated concentration, preferably 1.5 M to 8 M, more preferably 6 M. When urea is dissolved in a solvent as a denaturing agent, may be an aqueous solution of urea having a concentration of 2 M to saturated concentration, preferably 2 M to 10 M, more preferably 8 M.

The matrix may be used for conducting the above mass spectrometry step (ix). Therefore, the matrix is preferably selected from 4-CHCA (α-cyano-4-hydroxycinnamic acid), 3-CHCA (α-cyano-3-hydroxycinnamic acid), and 3H4NBA (3-hydroxy-4-nitrobenzoic acid) as described in the mass spectrometry step (ix). Also a set of 3H4NBA and 4-CHCA is preferred for use as the mixed matrix.

These matrices and auxiliary matrices may be dissolved in solvents as described in the mass spectrometry step (ix). For example, the matrix may be as a solution having a concentration of 1 mg/ml to saturated concentration. When an acetonitrile aqueous solution, TFA aqueous solution, or an acetonitrile-TFA aqueous solution is used as a solvent, α-cyano-3-hydroxycinnamic acid may be as a solution having a concentration of 1 mg/ml to saturated concentration, preferably 10 mg/ml; 3-hydroxy-4-nitrobenzoic acid may be as a solution having a concentration of 1 mg/ml to saturated concentration, preferably saturated concentration; and α-cyano-4-hydroxycinnamic acid may be as a solution having a concentration of 1 mg/ml to saturated concentration, preferably 10 mg/ml. Also, a mixed solution in which a solution of 3-hydroxy-4-nitrobenzoic acid and a solution of a-cyano-4-hydroxycinnamic acid, among these solutions, in a volume ratio of preferably 1:10 to 10:1, more preferably 1:3 to 3:1, for example 1:1 is exemplified.

The kit of the present invention may further contain a desalting column and filling gel for the desalting column; a reduction reagent and an alkylation reagent; trypsin; and a column for filling the media having a phenyl group. The desalting column and filling gel for the desalting column may be used for conducting the above desalting step (iv), for example. The reduction reagent and the alkylation reagent may be used for conducting the above reduction and alkylation step (vi), for example. Trypsin may be used for conducting the above digestion step (vii), for example. The column for filling the media having a phenyl group may be used for conducting the enrichment/separation step (viii), for example. In other words, the column for filling the media having a phenyl group may be used as an enrichment column, and the media having a phenyl group may be used as filling gel for the enrichment column.

The kit of the present invention enables to conduct a global quantitative analysis of protein of the present invention as described above, and therefore, brings the following effect as already described in the method of the present invention.

Decrease in sample loss
Reduction of +57(m/z) band
Reduction in rate of mingled unmodified peptides
Improvement in separating efficiency of each peptide
Realization of MS/MS analysis using QIT
Increase in number of detectable pair of peaks
Shortening in total operation time for the protocol
Improvement in quantitiativeness

EXAMPLES

Experimental Examples exhibited the effects of the present invention using a part or the whole of the protocol of the present invention are shown below.

Experimental Example 1

As a model protein, each 25 μg of purified four kinds of proteins (ovalbumin (Ova), glycelaldehyde-3-phosphate dehydrogenase (G3P), lysozyme (Lys) and α-lactalbumin α-lact), each available from SIGMA) were prepared and mixed together to give a total of 100 μg of Control sample (C).

Two kinds of Samples (S) were prepared. One of Samples (S) was prepared as follows. Namely, 100 μg of protein mixture as same as Sample (C) was solubilized with 0.1 w/v % SDS aqueous solution containing 5 mM EDTA according to the conventional NBS protocol followed by heating at 100° C. for 3 minutes, modification using an NBS(light) reagent and desalting using an LH-20 column. It is to be noted that "solubilization" referred in the present Experimental Example and following Experimental Examples is a different step from the solubilization generally conducted for preparing a sample of SDS-PAGE.

The other of Samples (S) was prepared in the following manner. 100 μg of protein mixture as same as Sample (C) was subjected to SDS solubilization in the same manner as described above, and modified with an NBS(light) reagent. Another 100 μg of protein mixture as same as Sample (C) was subjected to SDS solubilization in the same manner as described above, and modified with an equal amount of an NBS(heavy) reagent to the above NBS(light) reagent. The resultant NBS(light)-modified sample and NBS(heavy)-modified sample were mixed and desalted with an LH-20 column.

Two kinds of Samples (G) were separately prepared. These samples were prepared in the same manner as in Samples (S) except that solubilization was conducted using 6 M guanidine hydrochloride aqueous solution containing 5 mM EDTA as in the protocol of the present invention.

Two kinds of Samples (U) were separately prepared. These samples were prepared in the same manner as in Samples (S) except that solubilization was conducted using 8 M urea aqueous solution containing 5 mM EDTA as in the protocol of the present invention.

Samples (C), (S), (G), and (U) obtained in the manner as described above were subjected to electrophoresis. As to Samples (C), an amount corresponding to its 10 µg was developed on Lane 1. As to each of Samples (S), (G), and (U), an amount corresponding to its 1/20 was developed (Lanes 2 to 7).

The result of electrophoresis is shown in FIG. 1. Lane 1 is for Control sample (C); Lane 2 is for Sample (S) containing only NBS(light)-modified protein; Lane 3 is for Sample (G) containing only NBS(light)-modified protein; Lane 4 is for Sample (U) containing only NBS(light)-modified protein; Lane 5 is for Sample (S) in which equal amounts of NBS(light)-modified protein and NBS(heavy)-modified protein are mixed; Lane 6 is for Sample (G) in which equal amounts of NBS(light)-modified protein and NBS(heavy)-modified protein are mixed; and Lane 7 is for Sample (U) in which equal amounts of NBS(light)-modified protein and NBS(heavy)-modified protein are mixed. As shown by the results of Lanes 3, 4, 6, and 7 in FIG. 1, it is proven to be possible to keep the solubility with least loss of the sample when guanidine hydrochloride or urea serving, both of which are denaturing agents, is used for solubilization.

Experimental Example 2

100 µg of mouse (C57BL) serum was prepared as Control sample (C).

Two types of Samples (S) were separately prepared. One of Samples (S) was prepared in the following manner. Namely, 100 µg of mouse serum as same as Sample (C) was solubilized with a 0.1 w/v % SDS aqueous solution containing 0.5 mM EDTA followed by heating at 100° C. for 3 minutes according to the conventional NBS protocol, and modified with an NBS (light) reagent. Another 100 µg of mouse serum as same as Sample (C) was subjected to SDS solubilization in the same manner as described above, and modified with an equal amount of an NBS(heavy) reagent to the above NBS (light) reagent. The resultant NBS (light)-modified sample and NBS(heavy)-modified sample were mixed together to obtain a modified mixture.

The other of Samples (S) was prepared in the following manner. Namely, from 100 µg of mouse serum, a modified mixture was prepared in the same manner as described above, which was further subjected to desalting by an LH-20 column.

Two types of Samples (G) were separately prepared. These samples were prepared in the same manner as in Samples (S) except that solubilization was conducted using 6 M guanidine hydrochloride aqueous solution containing 5 mM EDTA as in the protocol of the present invention.

Two types of Samples (U) were separately prepared. These samples were prepared in the same manner as in Samples (S) except that solubilization was conducted using 8 M urea aqueous solution containing 5 mM EDTA as in the protocol of the present invention.

Samples (C), (S) (U), and (G) obtained were subjected to electrophoresis. As to Samples (C), an amount corresponding to its 10 µg was developed on Lane 2, and an amount corresponding to its 2 µg was developed on Lane 3. As to each Samples (S), (U), and (G), an amount corresponding to its 1/20 was developed (Lanes 4 to 9).

Figure 2:
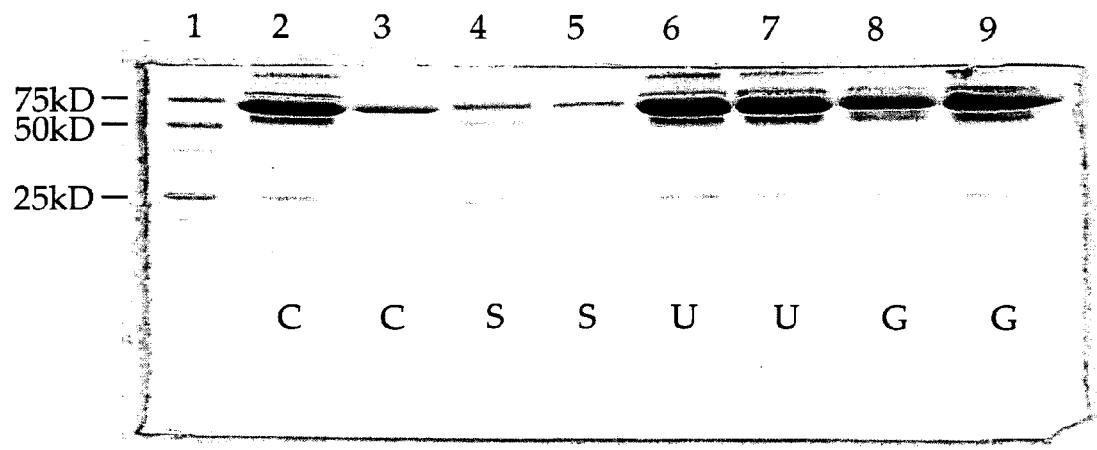
FIG. 2 is an electrophoretic diagram obtained in Experimental Example 2.

The result of electrophoresis is shown in FIG. 2. In FIG. 2, Lane 1 is for a molecular weight marker; Lane 2 and 3 are for Control sample (C); Lane 4 is for Sample (S) after modification; Lane 5 is for Sample (S) after modification and desalting; Lane 6 is for Sample (U) after modification; Lane 7 is for Sample (U) after modification and desalting; Lane 8 is for Sample (G) after modification; and Lane 9 is for Sample (G) after modification and desalting. As shown by the results of Lanes 6, 7, 8, and 9 in FIG. 2, it is proven to be possible to keep the solubility with least loss of the sample when guanidine hydrochloride or urea serving, both of which are denaturing agents, is used for solubilization.

Experimental Example 3

An extract of mouse liver was used as an analyzing sample. With respect to this analyzing sample, solubilization by SDS, modification, desalting, resolubilization by SDS, reduction and alkylation, and digestion were conducted according to the conventional NBS protocol. With respect to another analyzing sample, solubilization by urea, modification, desalting, resolubilization by urea, reduction and alkylation, and digestion were conducted according to the protocol of the present invention. In any modification operation, on the one hand the solubilized sample was modified with an NBS(light) reagent; on the other hand the same amount of solubilized sample was modified with an equal amount of an NBS(heavy) reagent to the NBS(light) reagent; and then the both of the resulting modified samples were mixed. In the following Experimental Examples, modification operation is executed in the same manner. Each obtained sample was subjected to separation of NBS modified peptide using the phenyl column (column available from Amersham Biosciences: HiTrap phenyl). Elution was conducted by a stepwise concentration gradient (concretely, 7 levels of concentrations of 5% interval between 10% to 40%) of acetonitrile. Two fractions were assigned to each concentration.

Each elution fraction (EL1 to EL14) was analyzed using an AXIMA-CFR. The numbers of observed pairs of peaks are listed in Table 1. In the Table, (a) is a result by the method using SDS, and (b) is a result by the method using urea.

TABLE 1

|  | (a) SDS | (b) Urea |
| --- | --- | --- |
| EL1 | 2 | 8 |
| EL2 | 2 | 11 |
| EL3 | 2 | 17 |
| EL4 | 3 | 20 |
| EL5 | 2 | 25 |
| EL6 | 3 | 16 |
| EL7 | 4 | 18 |
| EL8 | 5 | 24 |
| EL9 | 4 | 12 |
| EL10 | 4 | 10 |
| EL11 | 2 | 5 |
| EL12 | 1 | 1 |
| EL13 | 0 | 3 |
| EL14 | 2 | 4 |
| total | 14 | 76 |

Figure 3:
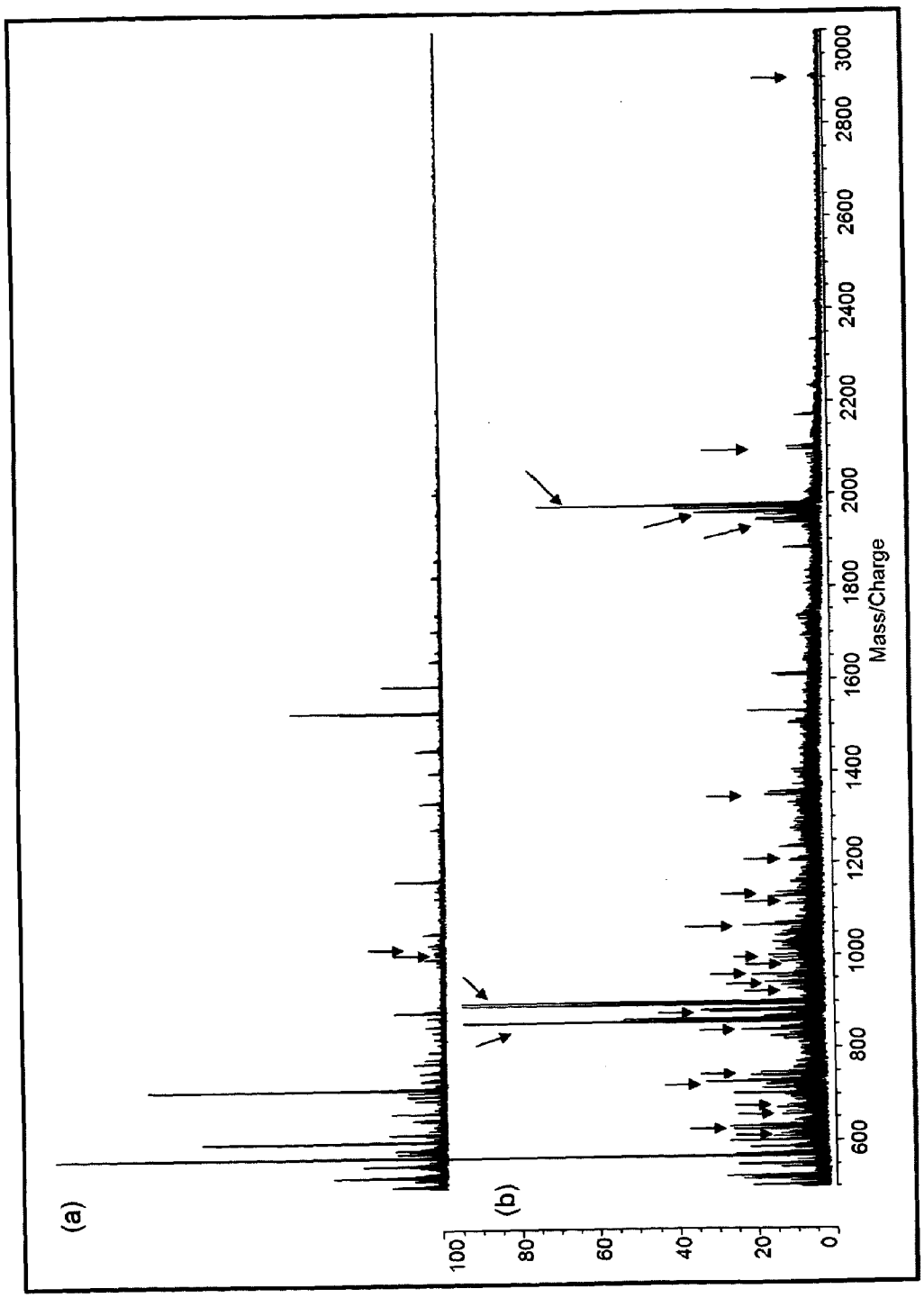
FIG. 3 is MS spectra for the fraction EL5 of an extract derived from mouse liver in Experimental Example 3, in which (a) shows a result by the method using SDS, and (b) shows a result by the method using urea.

As shown in this Table, a total of 76 pairs of peaks were observed in the method using urea according to the protocol of the present invention, as contrast with a total of 14 pairs of peaks observed in the method using SDS according to the conventional NBS protocol. Further, mass spectra for the fraction EL5 (namely acetonitrile concentration: 20%) in the Table are shown in FIG. 3(a) and FIG. 3(b). The peaks indicated by the arrows in Figures are pairs of peaks of modified peptides.

Experimental Example 4

A mixture of three kinds of purified proteins (G3P, Lys, and α-lact) was used as a model protein. The mixture was subjected to solubilization by SDS, modification, desalting, resolubilization by SDS, reduction and alkylation, and digestion according to the conventional NBS protocol. Separately the mixture was subjected to solubilization by guanidine hydrochloride, modification, desalting, resolubilization by guanidine hydrochloride, reduction and alkylation, and digestion were conducted according to the protocol of the present invention. Further separately the mixture was subjected to the same operation as described above according to the protocol of the present invention except that urea was used for solubilization. Each obtained sample was subjected to separation of NBS-modified peptide using a phenyl column, and MS analysis was performed.

With regard to the obtained MS spectra, an area ratio of monoisotopic peaks of each pairs of peaks was quantified and compared. Concretely, in each pair of peaks, a relative area of a smaller peak when an area of larger peak was defined as 100 was determined, which was used as an index of quantification to compare both of the obtained spectra. The result is shown in Table 2. As shown in Table 2, when guanidine hydrochloride (GdnHCl) and urea were used according to the protocol of the present invention, an average value of a relative area of peak was respectively 90.0 and 92.0, as compared with an average value of 80.3 obtained by the method using SDS according to the conventional NBS protocol. This shows that quantitativeness is significantly improved by the present invention.

TABLE 2

| | | area ratio of pairs of peaks | | |
|---|---|---|---|---|
| | m/z | GdnHCl | Urea | SDS |
| G3P | 627 | 92.5 | 93.1 | 96.5 |
| | 1916 | 83.7 | 93.1 | 61.8 |
| a-lact | 759 | 91.5 | 93.8 | 98.2 |
| | 1244 | 81.5 | 96.4 | 92.5 |
| | 1353 | 97 | 96.1 | 90.7 |
| Lys | 1198 | 97.3 | 98.9 | 72.3 |
| | 1299 | 93.8 | 80.2 | 78.7 |
| | 1478 | | 95.6 | 63.0 |
| | 1981 | 82.3 | 86 | 68.9 |
| average | | 90.0 | 92.6 | 80.3 |
| variance | | 37.1 | 30.5 | 186.4 |
| standard deviation | | 6.1 | 5.5 | 13.7 |

Additionally, variance and standard deviation of area ratio of pairs of peaks were determined. The results are also shown in Table 2. As shown in Table 2, variance was respectively 37.1 and 30.5 by the method using guanidine hydrochloride and urea according to the protocol of the present invention, as compared with 186.4 obtained by the method using SDS according to the conventional protocol. On the other hand, standard deviation was respectively 6.1 and 5.5, by the method using guanidine hydrochloride and urea according to the protocol of the present invention, as compared with 13.7 obtained by the method using SDS according to the conventional protocol. The smaller the values of variance and standard deviation are, the smaller the data variation is. Therefore, it was also demonstrated that the present invention greatly improved data variation.

Experimental Example 5

Figure 4:
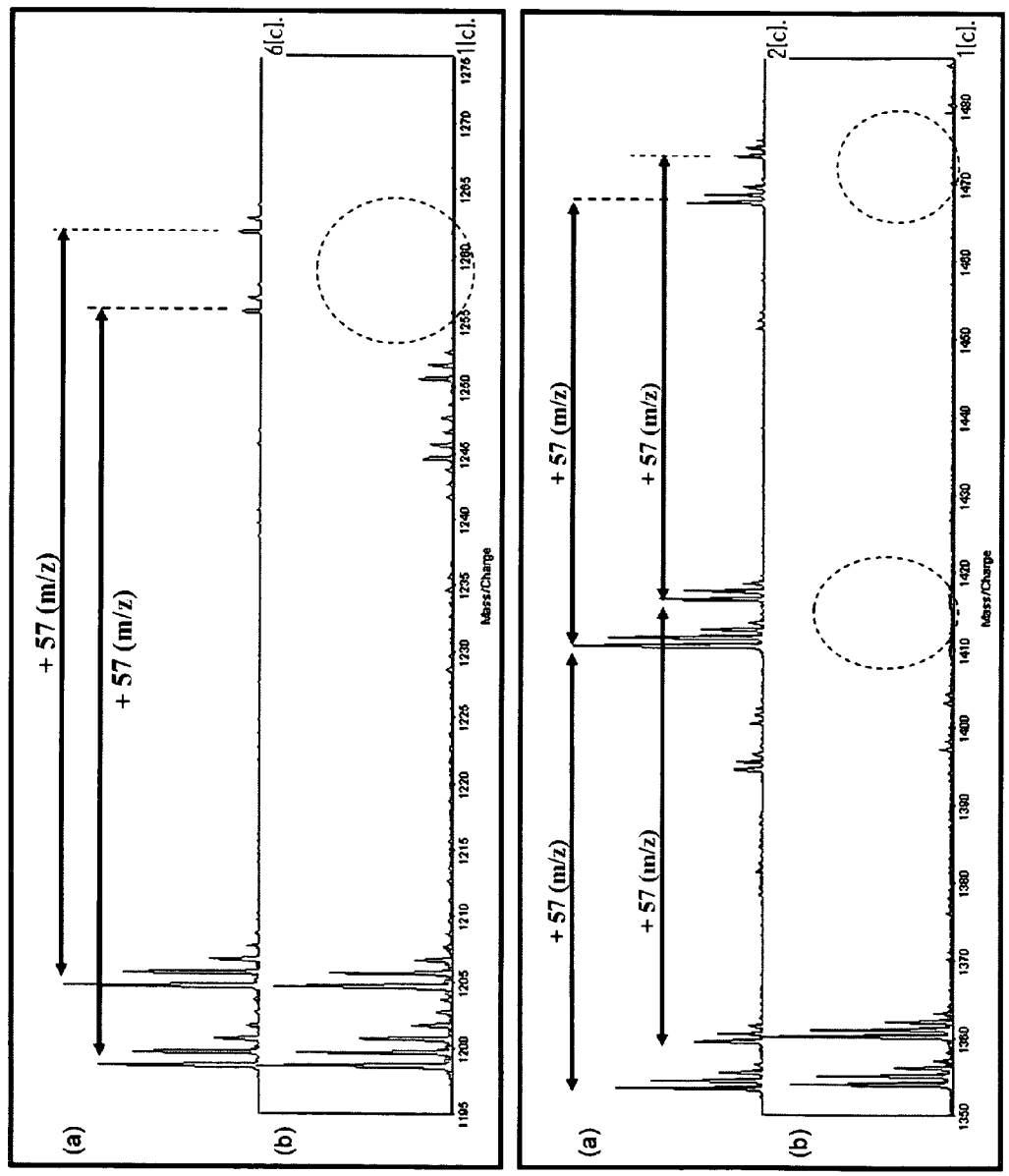
FIG. 4 is MS spectra of a sample derived from a mixture of Ova, G3P, Lys, and α-lact in Experimental Example 5, in which (a) shows a result for the sample obtained according to the conventional NBS Protocol, and (b) shows a result for the sample obtained according to the protocol of the present invention.

Using a mixture of four kinds of purified proteins (Ova, G3P, Lys, and α-lact) as a protein model, solubilization, modification, desalting, resolubilization, reduction and alkylation, and digestion were conducted according to the conventional NBS protocol. On the other hand, using the same protein model, solubilization by urea, modification, desalting, resolubilization by urea, reduction and alkylation, and digestion were conducted according to the protocol of the present invention. Further, both of the resultant samples were fractionated respectively using a phenyl column. From the sample prepared by operating according to the conventional NBS protocol, one fraction was collected, and from the sample prepared by operating according to the protocol of the present invention, a fraction corresponding to the above one fraction was collected. Each collected fraction was analyzed using an AXIMA-CFR. The results are shown in FIG. 4(a) and FIG. 4(b). FIG. 4(a) shows a result for the sample obtained according to the conventional NBS protocol, and FIG. 4(b) shows a result for the sample obtained according to the protocol of the present invention. In these FIGS., the horizontal axis represents mass-to-charge ratio, and the vertical axis represents a relative intensity of ion. As shown by the results of FIG. 4, a +57(m/z) peak indicative of occurrence of alkylation which is a side reaction is detected in the conventional method, while such a peak is not detected in the method of the present invention.

Experimental Example 6

Figure 5:
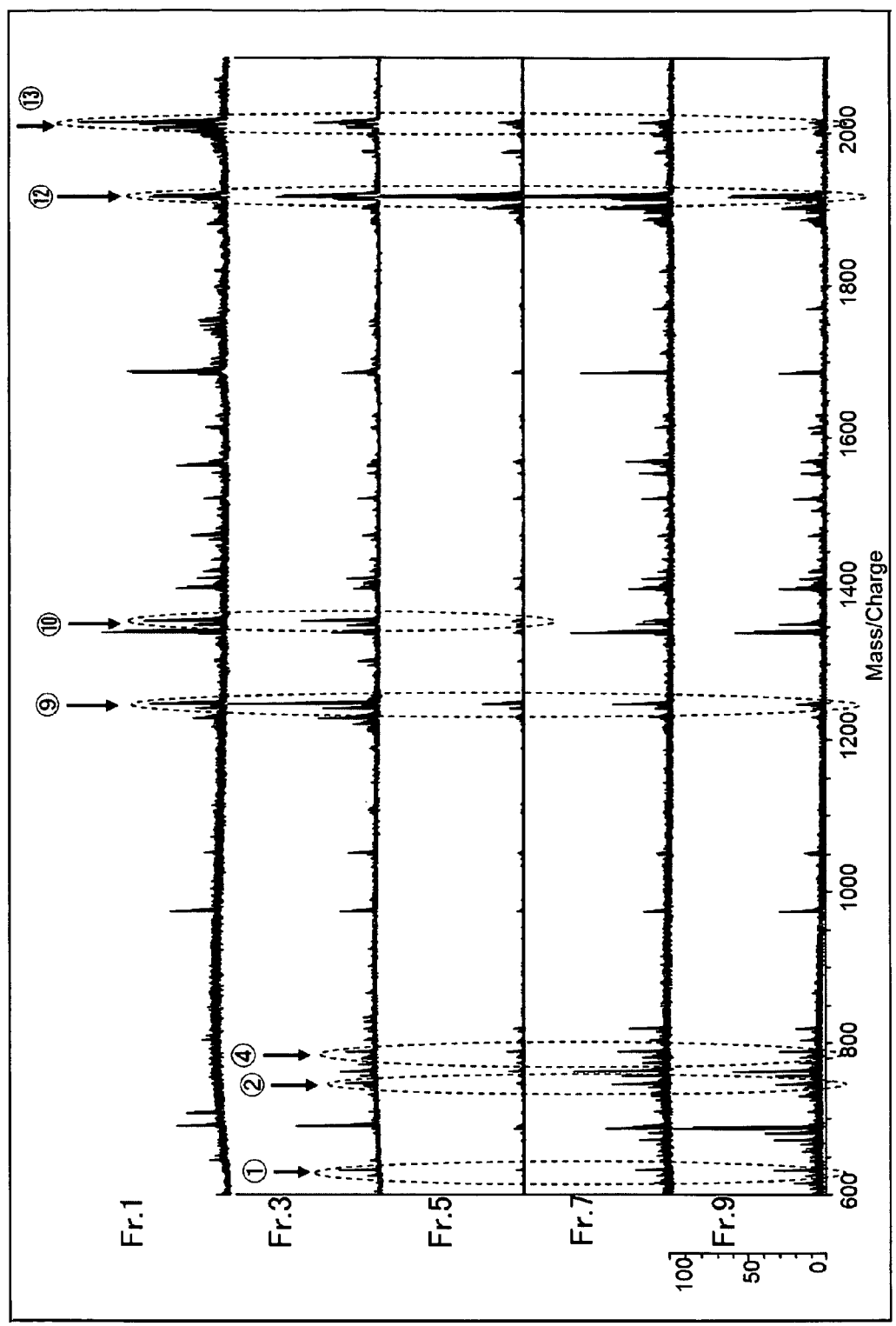
FIG. 5 is MS spectra obtained in Experimental Example 6.
Figure 6:
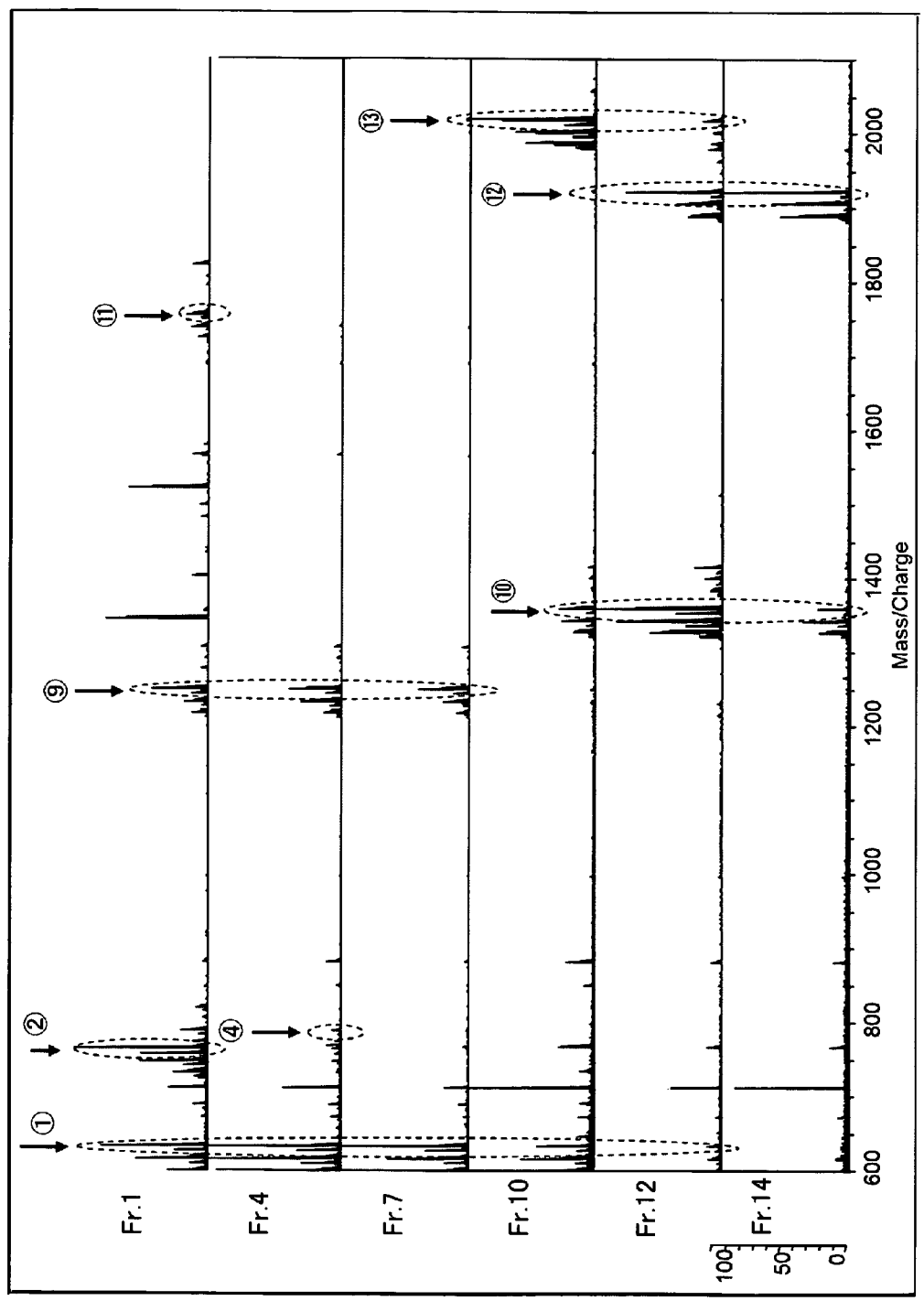
FIG. 6 is MS spectra obtained in Experimental Example 6.

Using a mixture of four kinds of purified proteins (Ova, G3P, Lys, and α-lact) as a protein model, solubilization, modification, desalting, resolubilization, reduction and alkylation, digestion, and separation of NBS-modified peptides using an enrichment column (LH-20) were conducted according to the conventional NBS protocol. A mass spectra of a representative eluted fraction is shown in FIG. 5. On the other hand, using the same protein model, solubilization by urea, modification, desalting, resolubilization by urea, reduction and alkylation, digestion, and separation of NBS-modified proteins using a phenyl column (column available from Amersham Biosciences: HiTrap phenyl) were conducted according to the protocol of the present invention. A mass spectra of a representative eluted fraction is shown in FIG. 6.

In these FIGS., the horizontal axis represents mass-to-charge ratio, and the vertical axis represents a relative intensity of ion. FIG. 5 shows results for the first, third, fifth, seventh, and ninth fractions (Fr.1, Fr.3, Fr.5, Fr.7, and Fr.9) among the total of 10 fractions obtained by the LH-20. FIG. 6 shows results for the first, fourth, seventh, tenth, twelfth, and fourteenth fractions (Fr.1, Fr.4, Fr.7, Fr.10, Fr.12, and Fr.14) among the total of 18 fractions obtained by the phenyl column. As shown by the results of FIG. 5 and FIG. 6, unmodified peptides that are observed a lot around m/z value of 1200 to 1700 in the conventional NBS method were hardly observed in the method of the present invention. Additionally, in FIG. 5, the first, second, fourth, ninth, tenth, twelfth, and thirteenth peptides (indicated by arrows in FIG.) were eluted in almost all of the eluted fractions for measurement, while in FIG. 6, such peptides were eluted while being separated to some extent.

Experimental Example 7

Figure 7:
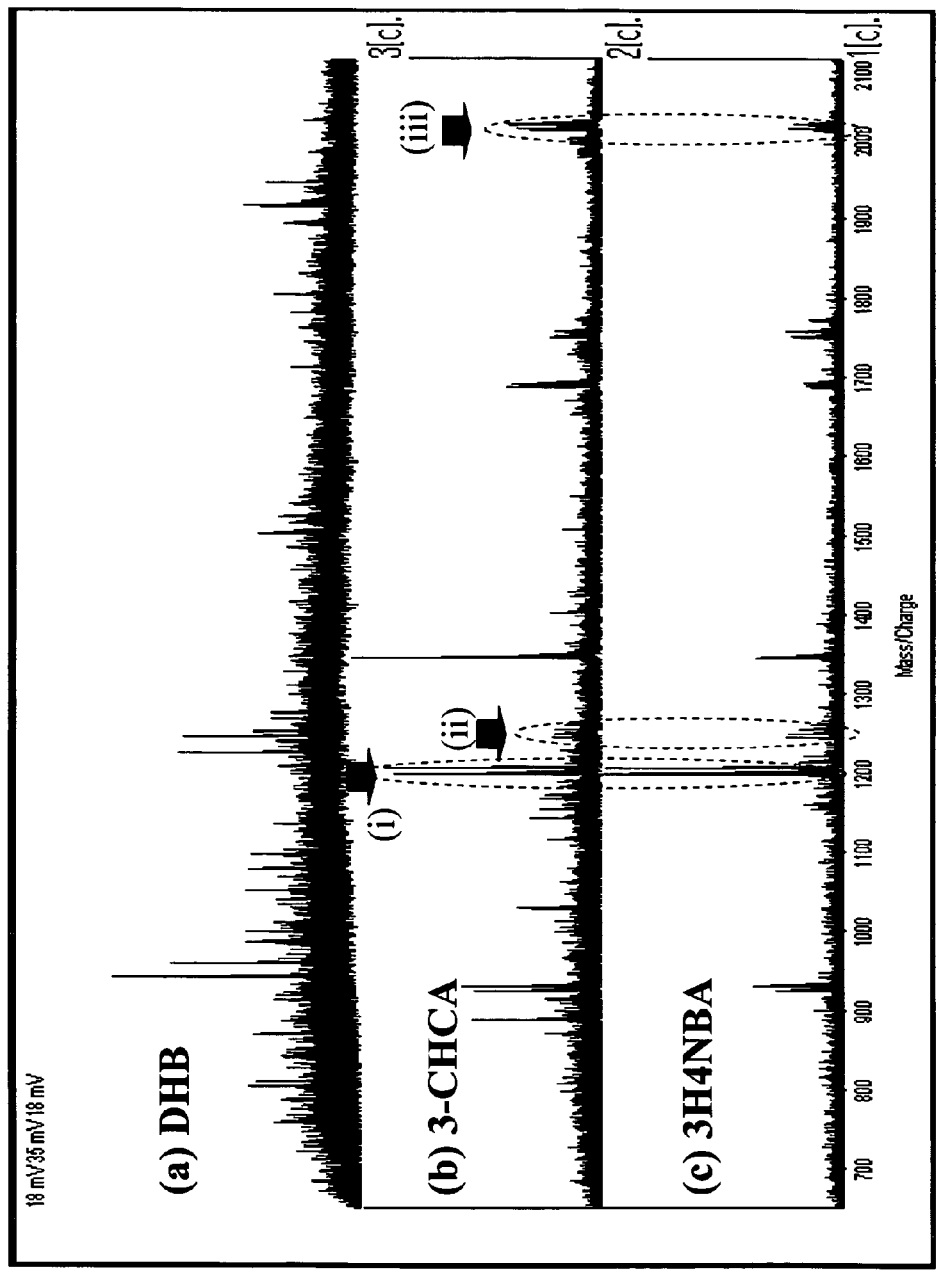
FIG. 7 is MS spectra of a sample derived from a mixture of Ova, G3P, Lys, and α-lact in Experimental Example 7, in which (a) shows a result by using matrix DHB, (b) shows a result by using matrix 3-CHCA, and (c) shows a result by using matrix 3H4NBA.

Using a mixture of four kinds of purified proteins (Ova, G3P, Lys, and α-lact) as a model protein, solubilization by urea, modification, desalting, resolubilization by urea, reduction and alkylation, digestion, and separation of NBS-modified peptides using a phenyl column were conducted according to the protocol of the present invention. Then one fraction eluted from the phenyl column was prepared as a sample for mass spectrometry, and mass spectrometry using an AXIMA-QIT was conducted using respective following three matrices. As matrix, three kinds of matrices: DHB that is conventionally used, and 3-CHCA and 3H4NBA that are used in the present invention were used; and, each of DHB and 3-CHCA was used as a solution of 10 mg/ml and 3H4NBA was used as a saturated solution, respectively in a solvent of 50% acetonitrile aqueous solution containing 0.1% TFA. Equal amounts of the prepared sample and the matrix solution were mixed and subjected to measurement using an AXIMA-QIT. The results are shown in FIGS. 7(a) to 7(c).

Figure 8:
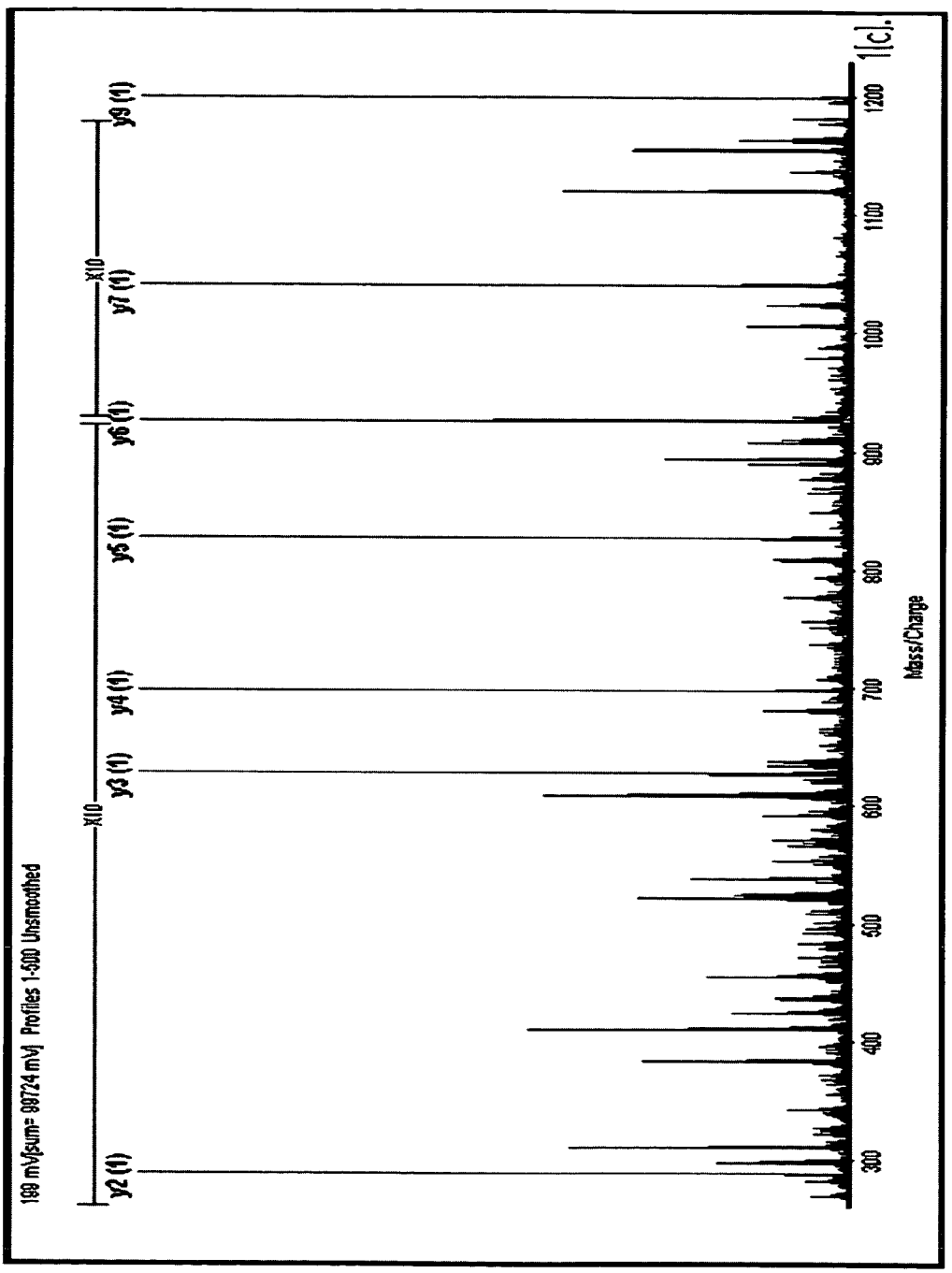
FIG. 8 is a MS spectrum obtained in Experimental Example 7.

In these FIGS., the horizontal axis represents mass-to-charge ratio, and the vertical axis represents a relative intensity of ion. The peaks indicated by the arrows (i) to (iii) in FIGS. 7(b) and 7(c) are pairs of peaks of modified peptides. As shown in FIGS. 7(a) to 7(c), when DHB was used as a matrix (FIG. 7(a)), NBS-modified peptides were hardly ionized so that they were not detected on the mass spectrum. Contrarily, when 3-CHCA (FIG. 7(b)) and 3H4NBA (FIG. 7(c)) were used, NBS-modified proteins were efficiently ionized so that there were detectable on the mass spectra. Further, the result of MS/MS analysis, of the ion for the peak at m/z value of 1198.53 corresponding to an NBS(light)-modified peptide in the pairs of peaks indicated by the arrow (i) obtained in FIG. 7B, is shown in FIG. 8.

Experimental Example 8

In the present Experimental Example, measurement was conducted by means of a mass spectrometers using a mixture of peptides modified with NBS reagent and unmodified peptides as a sample to be measured, and using a mixed matrix containing 3H4NBA and 4-CHCA.

The sample to be measured was prepared in the following manner.

Two sample mixtures each having a total weight of 100 μg given by each 25 μg of four purified proteins (ovalbumin, glyceraldehyde-3-phosphate dehydrogenase, lysozyme, and α-lactalbumin, all available from SIGMA) was mixed were prepared. The protocol for "$^{13}$CNBS Isotope Labeling Kit" (SHIMADZU) was followed except that solubilization of each mixture and resolubilization of NBS-modified sample mixture was conducted using urea having a final concentration of 8M as a denaturing agent. Specifically, One sample mixture was labeled-modified with a NBS Reagent (heavy) (2-nitro[$^{13}$C$_6$] benzenesulfenyl chloride), and the other sample mixture was nonlabeled-modified with a NBS Reagent (light) (2-nitro[$^{12}$C$_6$] benzenesulfenyl chloride). Mixing of the both of the modified samples, desalting, resolubilization by urea, reduction, alkylation, and trypsin digestion were conducted. The samples after digestion were conducted desalting treatment with ZipTip μ-C18, and eluting with 4 μl of 50% acetonitrile aqueous solution containing 0.1% TFA, to obtain a sample to be measured. 0.5 μl from this sample was applied on a target plate.

The matrix for use was prepared in the following manner. Each of 3H4NBA and 4-CHCA was dissolved in a solvent of 50% acetonitrile aqueous solution containing 0.1% TFA. 3H4NBA was prepared into a saturation solution, and 4-CHCA was prepared into a solution of 10 mg/ml. These solutions thus prepared were mixed with each other in a volume ratio of 1:1 to obtain a mixed matrix solution. On a prepared target plate on which a sample to be measured was applied, 0.5 μL of the mixed matrix solution was added. After drying, measurement was conducted using a MALDI-IT-TOF mass spectrometer having an ion trap (AXIMA-QIT, SHIMADZU) and a MALDI-TOF mass spectrometer without an ion trap (AXIMA-CFR plus, SHIMADZU).

Figure 9:
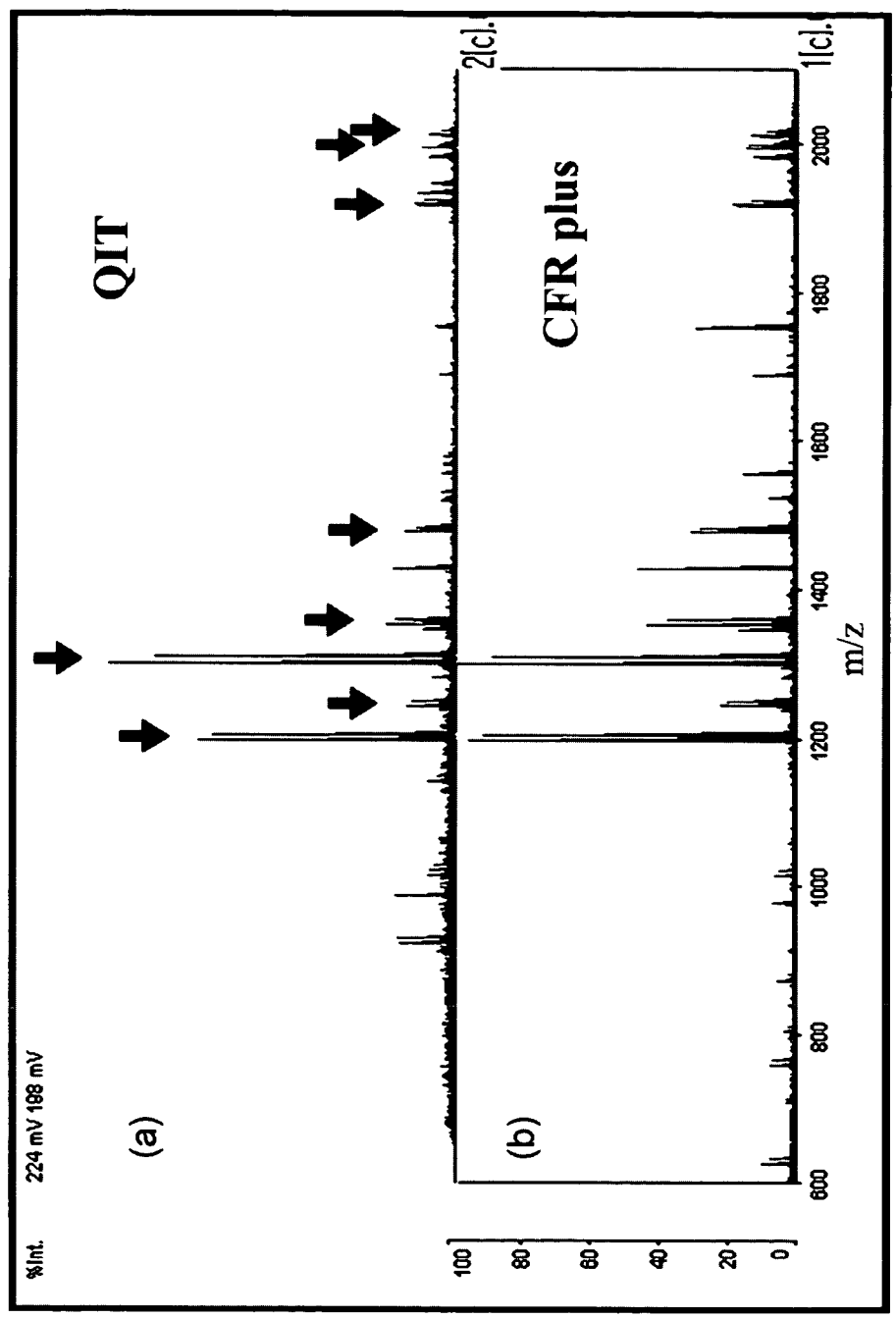
FIG. 9 is MS spectra of a sample derived from a mixture of Ova, G3P, Lys, and α-lact in Experimental Example 8, in which (a) is a spectrum obtained by using the AXIMA-QIT having an ion trap, and (b) is a spectrum obtained by using the AXIMA-CFR plus without an ion trap.

The MS spectra obtained in these measurements are shown in FIG. 9. In FIG. 9, the horizontal axis represents mass-to-charge ratio (m/z), and the vertical axis represents relative intensity of ion (% int.). (a) is a spectrum obtained by using the AXIMA-QIT having an ion trap, and (b) is a spectrum obtained by using the AXIMA-CFR plus without an ion trap. In FIG. 9, the peaks of pairs marked with the arrows come from NBS-modified peptides. Each pair of peaks has a difference of m/z value of 6 that is corresponding to a difference in mass between the two modification reagents, that is, between the NBS Reagent (heavy) (2-nitro [$^{13}$C6] benzenesulfenyl chloride) and the NBS Reagent (light) (2-nitro[$^{12}$C$_6$] benzenesulfenyl chloride).

As can be seen by comparison of the spectra of FIG. 9 (a) and (b), almost the same spectrum was obtained. The fact that almost the same spectrum was obtained by a mass spectrometer having an ion trap and by a mass spectrometer without an ion trap indicates that self-disintegration of the analyte is suppressed in measurement using a mass spectrometer having an ion trap. This leads the conclusion that the matrix mixture of the present invention suppresses self-disintegration of an analyte to be measured that occurs during conventional measurement using a mass spectrometer with an ion trap (namely, mass spectrometer requiring relatively long time from ionization to detection of ion) using 4-CHCA alone as a matrix. Further, almost of the detected peaks were pairs of peaks of NBS-modified peptide, which shows that the ability to detect with specificity possessed by the matrix 3H4NBA alone is maintained even in using the mixed matrix.

Experimental Example 9

In the present Experimental Example, using the same sample to be measured as Experimental Example 8, a mass spectrometry was conducted with a matrix of 3H4NBA by itself and a mixed matrix of 3H4NBA and 4-CHCA.

Using the same sample to be measured as Experimental Example 8, 4 μl of eluate was obtained as a sample to be measured in the same manner as Experimental Example 8. The sample to be measured was diluted in 0.1% TFA aqueous solution to make a 1000-fold dilution, and 0.5 μl from the diluted solution was applied on a target plate.

As the matrix, a matrix of 3H4NBA by itself and a mixed matrix in which 3H4NBA and 4-CHCA is combined were used.

The matrix of 3H4NBA by itself was prepared as a saturated solution by dissolving 3H4NBA in 50% acetonitrile aqueous solution containing 0.1% TFA. On a prepared target plate on which a sample to be measured was applied, the 3H4NBA solution was applied. After drying, measurement was conducted using a MALDI-TOF (AXIMA-CFR plus, SHIMADZU).

The mixed matrix of 3H4NBA and 4-CHCA was prepared in the same manner as in Experimental Example 8. On a prepared target plate on which a sample to be measured was applied, this mixed solution was applied. After drying, measurement was conducted using a MALDI-TOF (AXIMA-CFR plus, SHIMADZU).

Figure 10:
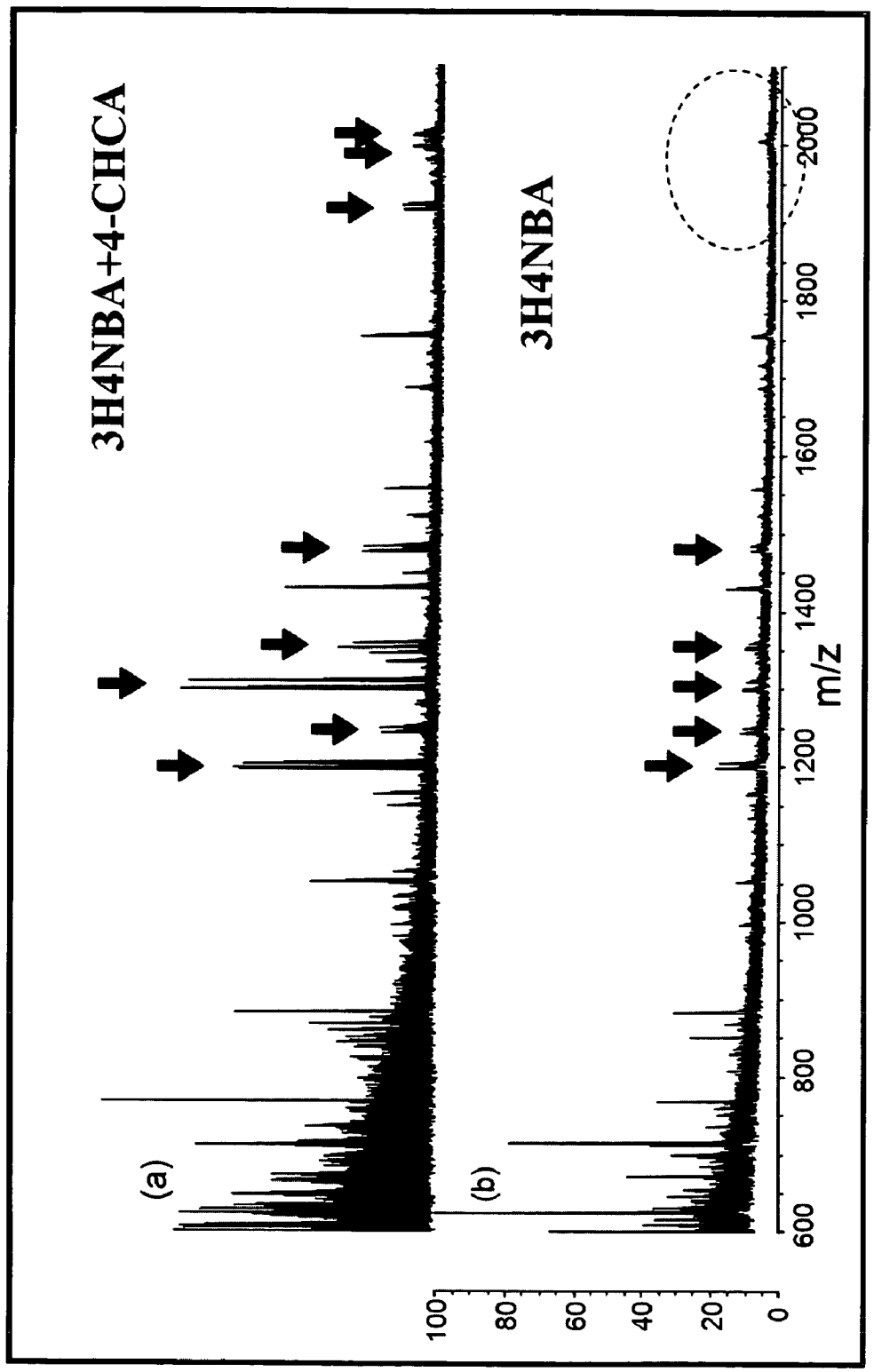
FIG. 10 is MS spectra of a sample derived from a mixture of Ova, G3P, Lys, and α-lact in Experimental Example 9, in which (a) is a spectrum obtained by using the mixed matrix of 3H4NBA and 4-CHCA. and (b) is a spectrum obtained by using the 3H4NBA matrix.

The MS spectra obtained in these measurements are shown in FIG. 10. In FIG. 10, the horizontal axis represents mass-to-charge ratio (m/z), and the vertical axis represents relative intensity of ion (%). (a) is a spectrum obtained by using the mixed matrix of 3H4NBA and 4-CHCA, and (b) is a spectrum obtained by using the 3H4NBA matrix. Further, FIG. 10 shows that the pairs of peaks marked with the arrows come from NBS-modified peptides. Each pair of peaks has a difference of m/z value of 6 that is corresponding to a difference in mass between the two modification reagents, that is, between the NBS Reagent (heavy) (2-nitro [$^{13}C_6$] benzenesulfenyl chloride) and a NBS Reagent (light) (2-nitro[$^{12}C_6$] benzenesulfenyl chloride).

As is apparent from comparison of spectra FIGS. 10(a) and (b), the pairs of peaks of NBS-modified peptides are detected more sensitively in (a) than (b). This indicates that sensitivity is improved when 3H4NBA is mixed with 4-CHCA as a matrix. It was confirmed that advantages of 4-CHCA that "measurement with high sensitivity can realize" in the condition that "optimum spot on which a laser beam is to be focused can be readily found" are added while keeping the advantage of 3H4NBA that "NBS-modified peptides can be detected selectively by mass spectrometry."

From the combined results of the above Experimental Example 8 and Experimental Example 9, it was confirmed that the advantage of 3H4NBA that "NBS-modified peptides can be detected selectively by mass spectrometry" and that "self-disintegration of analyte can be suppressed even if measurement is conducted using an ion trap type MALDI mass spectrometer in which the time from ionization to detection of ion is relatively long" and the advantage of 4-CHCA that "measurement with high sensitivity can realize" in the condition that "optimum spot on which a laser beam is to be focused can be readily found" were achieved simultaneously.

Experimental Examples 3, 4, 5 and 7 among the above described Experimental Examples show concrete modes within the scope of the present invention, however, the present invention can be carried out in various other modes. Therefore, the above-described Experimental Examples are merely illustrative in all respects, and must not be construed as being restrictive. Further, the changes that fall within the equivalents of the claims are all within the scope of the present invention.

What is claimed is:

1. A method for global quantitative analysis of protein comprising the steps of:
   (i) preparing two states of protein samples, a Protein sample I for analysis and a control Protein sample II;
   (ii) solubilizing the Protein sample I in a solution containing urea as a denaturing agent or in a solution containing guanidine hydrochloride as a denaturing agent, to obtain a solubilized Protein sample I, and separately solubilizing the Protein sample II in a solution containing urea as a denaturing agent or in a solution containing guanidine hydrochloride as a denaturing agent, to obtain a solubilized Protein sample II;
   (iii) subjecting the solubilized Protein sample I to modification reaction using either one of 2-nitro[$^{13}C_6$]benzenesulfenyl chloride and 2-nitro[$^{12}C_6$]benzenesulfenyl chloride, to obtain a modified Protein sample I, and separately subjecting the solubilized Protein sample II to modification reaction using the other one of 2-nitro [$^{13}C_6$]benzenesulfenyl chloride and 2-nitro[$^{12}C_6$]benzenesulfenyl chloride, to obtain a modified Protein sample II;
   (iv) mixing and desalting the modified Protein sample I and the modified Protein sample II, to obtain a desalted protein sample mixture;
   (v) resolubilizing the desalted protein sample mixture by using urea or guanidine hydrochloride, to obtain a resolubilized protein sample mixture;
   (vi) reducing and alkylating the resolubilized protein sample mixture, to obtain a reduced and alkylated protein sample mixture;
   (vii) subjecting the reduced and alkylated protein sample mixture to trypsin digestion in the presence of urea or guanidine hydrochloride, to obtain a peptide mixture containing modified peptide fragments and unmodified peptide fragments;
   (viii) separating the peptide mixture using a media having a phenyl group, to obtain enriched modified peptide fragments; and
   (ix) subjecting the enriched modified peptide fragments to mass spectrometry.

2. The method according to claim 1, wherein in the step (ix), the mass spectrometry is conducted using α-cyano-3-hydroxycinnamic acid or 3-hydroxy-4-nitrobenzoic acid as a matrix.

3. The method according to claim 2, wherein the matrix is used as a solution having a concentration of 1 mg/ml to a saturated concentration.

4. The method according to claim 1, wherein in the step (ix), when 3-hydroxy-4-nitrobenzoic acid is used as the matrix, the mass spectrometry is conducted using a mixed matrix of 3-hydroxy-4-nitrobenzoic acid and α-cyano-4-hydroxycinnamic acid.

5. The method according to claim 4, wherein α-cyano-4-hydroxycinnamic acid is used as a solution having a concentration of 1 mg/ml to a saturated concentration.

6. The method according to claim 5, wherein the solution of 3-hydroxy-4-nitrobenzoic acid and the solution of α-cyano-4-hydroxycinnamic acid are combined in a volume ratio of 1:10 to 10:1 to be used.

7. A kit containing 2-nitro[$^{13}C_6$]benzenesulfenyl chloride, 2-nitro[$^{12}C_6$]benzenesulfenyl chloride, and a media having a phenyl group.

8. A kit for carrying out the method according to claim 7, containing 2-nitro[$^{13}C_6$]benzenesulfenyl chloride, 2-nitro [$^{12}C_6$]benzenesulfenyl chloride, and a media having a phenyl group.

9. The kit according to claim 7, further containing a denaturing agent.

10. The kit according to claim 9, wherein the denaturing agent is urea or guanidine hydrochloride.

11. The kit according to claim 7, further containing α-cyano-3-hydroxycinnamic acid, 3-hydroxy-4-nitrobenzoic acid, or α-cyano-4-hydroxycinnamic acid as a matrix, or a mixture of 3-hydroxy-4-nitrobenzoic acid and α-cyano-4-hydroxycinnamic acid as a mixed matrix.

12. The kit according to claim 7, further containing at least one selected from the group consisting of a desalting column, filling gel for a desalting column, a reduction reagent, an alkylation reagent, trypsin, and a column for filling the media.

* * * * *